United States Patent
Tsuchiya et al.

(10) Patent No.: US 7,232,560 B2
(45) Date of Patent: Jun. 19, 2007

(54) UTILIZATION ABSORBER, COSMETIC AND METHOD FOR ENHANCING STABILITY OF ULTRAVIOLET-ABSORBING SUBSTANCES

(75) Inventors: Tsuyoshi Tsuchiya, Kanagawa (JP); Satoko Kozui, Kanagawa (JP)

(73) Assignee: The Nisshin Oillio Group, Ltd., Tokyo (JP)

( * ) Notice: Subject to any disclaimer, the term of this patent is extended or adjusted under 35 U.S.C. 154(b) by 191 days.

(21) Appl. No.: 10/470,998

(22) PCT Filed: Feb. 1, 2002

(86) PCT No.: PCT/JP02/00816

§ 371 (c)(1),
(2), (4) Date: Aug. 1, 2003

(87) PCT Pub. No.: WO02/062744

PCT Pub. Date: Aug. 15, 2002

(65) Prior Publication Data

US 2004/0067207 A1    Apr. 8, 2004

(30) Foreign Application Priority Data

Feb. 6, 2001    (JP)    ............... 2001-029116

(51) Int. Cl.
*A61K 8/00*    (2006.01)
*A61K 8/18*    (2006.01)
*A61K 31/355*    (2006.01)
*A61Q 17/04*    (2006.01)
*A01N 43/16*    (2006.01)

(52) U.S. Cl. ............... 424/59; 424/60; 514/458

(58) Field of Classification Search ........... 424/59, 424/60, 401; 514/458
See application file for complete search history.

(56) References Cited

U.S. PATENT DOCUMENTS

| 4,144,325 A | * | 3/1979 | Voyt ............... 424/59 |
| 4,975,272 A | * | 12/1990 | Voyt ............... 424/59 |
| 5,208,012 A | * | 5/1993 | Sudo et al. ........... 424/59 |
| 5,547,658 A | * | 8/1996 | Hansenne et al. ........ 424/59 |

FOREIGN PATENT DOCUMENTS

| JP | 7-233046 | 9/1995 |
| JP | 9-104856 | 4/1997 |
| WO | WO 96/17624 | 6/1996 |

OTHER PUBLICATIONS

Machine translation of JP 7-233046 May 9, 1995.*
Derwent-Acc-No: 1998-003447 abstracting JP 62267214A Nov. 19, 1987 4 pages.*

* cited by examiner

*Primary Examiner*—Johann Richter
*Assistant Examiner*—Ernst Arnold
(74) *Attorney, Agent, or Firm*—Nixon & Vanderhye P.C.

(57) ABSTRACT

Use of δ-tocopherol for enhancing the heat stability and/or oxidation stability of a para-methoxycinnamic ester; an ultraviolet absorber comprising a para-methoxycinnamic ester, and an effective amount of δ-tocopherol to enhance its heat stability and/or oxidation stability; and a cosmetic comprising the above ultraviolet absorber.

δ-tocopherol enhances the heat stability and/or oxidation stability of the para-methoxycinnamic ester which is an ultraviolet-absorbing substance frequently used.

16 Claims, 2 Drawing Sheets

UTILIZATION ABSORBER, COSMETIC AND METHOD FOR ENHANCING STABILITY OF ULTRAVIOLET-ABSORBING SUBSTANCES

This application is the U.S. national phase of international application PCT/JP02/0816, filed Feb. 1, 2002, which designated the U.S.

TECHNICAL FIELD

This invention relates to use of a specific substance, an ultraviolet absorber and a cosmetic, the common object of which is to enhance the heat stability and/or oxidation stability of para-methoxy cinnamic esters mainly used as ultraviolet-absorbing components in general purpose cosmetics.

BACKGROUND ART

Ultraviolet rays reaching the surface of the earth are only 6% of the rays of the sun, but cause degradation in quality such as coloring, fading, lowering of strength, or destruction of rubbers, paints, inks, etc. For preventing such degradation caused by ultraviolet rays, ultraviolet absorbers are incorporated in various products into which these products and materials are compounded.

Also on human skin, ultraviolet rays cause skin acute reaction such as sun burn or sun tan, and, on a long-term basis, skin aging or cancer. In view of these points, development of sunscreen cosmetics in which an ultraviolet absorber or an ultraviolet-scattering agent is compounded has actively been made, and various preparations are sold.

Ultraviolet absorbers compounded in these preparations are classified, based on their structure, into cinnamic acid-type, PABA-type, benzophenone-type, salicylic acid-type, heterocyclic-type, camphor-type, dibenzoylmethane-type, chalcone-type, etc., and many ultraviolet absorbers have been developed. However, ultraviolet absorbers used for human skin are restricted in view of safety, touching in use, solubility thereof into the base in compounding in sunscreen cosmetics, etc., and among many so far developed ultraviolet absorbers, cinnamic acid-type and benzophenone-type ultraviolet absorbers are frequently used in skin external preparations.

As an invention which started from a motive of substituting a natural antioxidant for BHT in preparations being to contact with human bodies, an invention in which para-methoxycinnamic esters are stabilized using tocopherol is known (Japanese Laid-open Patent Publication 9-104856). Therein, it is only α-tocopherol that is specifically exemplified as the tocopherol.

Among cinnamic acid-type ultraviolet absorbers, ultraviolet absorbers containing a para-methoxycinnamic ester are mainly used, and as an example, 2-ethylhexyl para-methoxycinnamate is mentioned. Para-methoxycinnamic ester-type ultraviolet absorbers have a defect of being insufficient in stability with time lapse on smell, color, etc., and as their stabilizer, butylhydroxytoluene (BHT) is usually used. However, on the other hand, there is a trend that the addition of a stabilizer is not preferred, and both of BHT-added preparations and BHT-not added preparations are sold on the market.

However, butylhydroxytoluene (BHT) which has hitherto been used is a component on which the duty of indication is assigned among stabilizers in the cosmetic field, and although BHT is a stabilizer expected on its effect, it has an aspect of being hard to accept on the market in view of safety. Further, when no stabilizer is added, it is known that the prescribed preparation starts to deteriorate at an early stage on smell and/or color, and usually, the influence on the prescribed preparation increases together with time lapse. Therefore, when an ultraviolet absorber containing no stabilizer was prescribed, a treatment such as masking gets necessary, but in prescription of no perfume, there is a problem that such a treatment is hard to make.

Therefore, development of stabilizers whose component indication is not compelled and which have high safety has been desired.

DISCLOSURE OF INVENTION

In such actual situation, the present inventors intensely studied for finding a stabilizer whose component indication is not required and which has high safety, among components used as antioxidants like BHT. As a result, they found, unexpectedly, that δ-tocopherol has a better action of stabilizing para-methoxycinnamic esters than α-tocopherol, and completed this invention.

Namely, the invention relates to use of δ-tocopherol for enhancing the heat stability and/or oxidation stability of a para-methoxycinnamic ester; an ultraviolet absorber comprising a para-methoxycinnamic ester, and an effective amount of δ-tocopherol to enhance its heat stability and/or oxidation stability; and a cosmetic comprising the ultraviolet absorber.

BEST MODE FOR CARRYING OUT THE INVENTION

Figure 1:
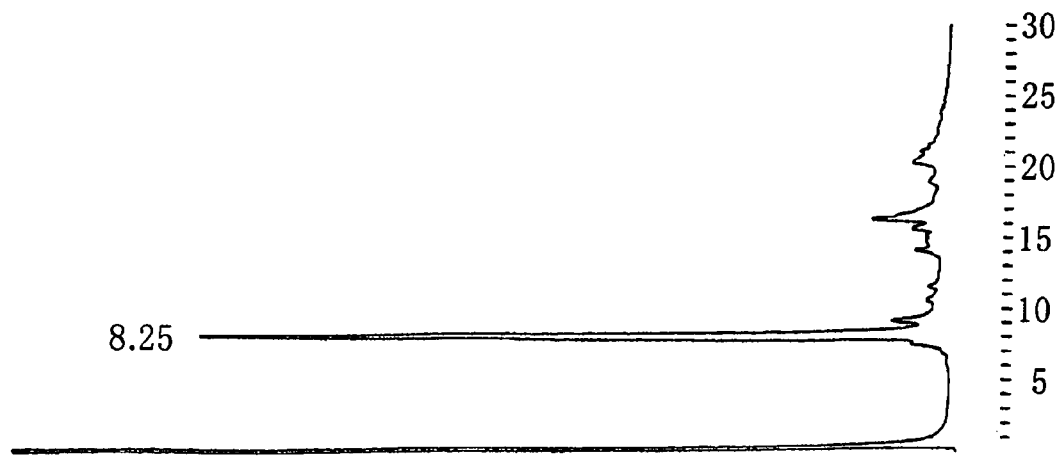
FIG. 1 shows the gas chromatogram of the measurement sample immediately after the CDM test on the case where δ-tocopherol was added in an amount of 0.01% by mass. Among the two large peaks, the peak appearing at the earlier time of the time co-ordinate is the peak of the sample-diluting solvent, and the peak appearing at the later time is the peak of 2-ethylhexyl para-methoxycinnamate (this is also the case with the following figures).

Para-methoxycinnamic esters used in the invention include alkyl para-methoxycinnamates, preferably alkyl para-methoxycinnamates in which the alkyl part is a straight-chain or branched-chain alkyl group having 1 to 18 carbon atoms, particularly 2 to 8 carbon atoms, and glycerol di-para-methoxycinnamate mono-2-ethylhexanoate, etc. Specifically as the above alkyl para-methoxycinnamates, there can for example be mentioned ethyl para-methoxycinnamate, isopropyl para-methoxycinnamate, isoamyl para-methoxycinnamate, 2-ethylhexyl para-methoxycinnamate, etc. These para-methoxycinnamic esters may be used alone. Most preferred among these para-methoxycinnamic esters is 2-ethylhexyl para-methoxycinnamate.

δ-tocopherol used in the invention may be natural one or synthesized one, but preferred is natural one. δ-tocopherol does not necessarily need to be pure, but is preferably one having a purity of 70% or more, more preferably one having a purity of 80% or more, and still further preferably one having a purity of 90% or more.

The invention first relates to use of δ-tocopherol for enhancing the heat stability and/or oxidation stability of a para-methoxycinnamic ester. In this use, it is necessary that the para-methoxycinnamic ester and the δ-tocopherol are in such a state that they can contact with each other, and the δ-tocopherol is present in an effective amount to enhance the heat stability and/or oxidation stability of the para-methoxycinnamic ester. As examples of such use, an ultraviolet absorber comprising both of them, and a cosmetic comprising such an ultraviolet absorber, as described later, but not limited thereto, any use of δ-tocopherol to enhance the heat stability and/or oxidation stability of a para-methoxycinnamic ester is included. The amount of δ-tocopherol effective to enhance the heat stability and/or oxidation stability of a para-methoxycinnamic ester in such use can appropriately be determined referring to the amount of δ-tocopherol in the ultraviolet absorber as described later.

The invention secondly relates to an ultraviolet absorber comprising a para-methoxycinnamic ester, and an effective amount of δ-tocopherol to enhance its heat stability and/or oxidation stability. Such ultraviolet absorber may consist of a para-methoxycinnamic ester and δ-tocopherol, but may further contain a diluting or bulking component and/or another ultraviolet absorbing substance.

The diluting or bulking component includes hydrocarbons such as paraffins, liquid paraffin, liquid isoparaffin, squalane and vaselines, animal and vegetable fats and oils such as lanolin, equine oil, soybean oil, olive oil, coconut oil, castor oil and macadamia nut oil, and their essential oils; wax esters such as jojoba oil, Japan wax and beeswax; fatty acids such as capric acid, caprylic acid, lauric acid, myristic acid, palmitic acid, stearic acid, behenic acid, oleic acid, isooctylic acid, isomyristic acid, isopalmitic acid, isostearic acid, hydroxystearic acid, ricinolic acid and coconut oil fatty acids; alcohols such as lauryl alcohol, myristyl alcohol, cetanol, stearyl alcohol, behenyl alcohol, isooctyl alcohol, isodecyl alcohol, isocetyl alcohol, isostearyl alcohol and octyldodecanol; vitamins and their derivatives such as vitamin A and vitamin C derivatives; synthetic esters such as cetyl octanoate, isopropyl myristate, glycerol tri-2-ethylhexanoate, octyldodecyl myristate, isooctyl palmitate, pentaerythritol tetra-2-ethylhexanoate and trimethylolpropane triisostearate; etc.

Other ultraviolet absorbing substances include methyl cinnamate, ethyl cinnamate, methyl 2,4-diisopropylcinnamate, ethyl 2,4-diisopropylcinnamate, octyl para-dimethylaminobenzoate, sodium para-methoxycinnamate, potassium para-methoxycinnamate, etc.

The content of the para-methoxycinnamic ester in the ultraviolet absorber of the invention is not particularly limited so long as it is such an amount that necessary ultraviolet absorption effect can be attained, but the content is preferably 50% by mass or more, more preferably 70% by mass or more, most preferably 95% by mass or more.

The content of δ-tocopherol in the ultraviolet absorber of the invention is not particularly limited so long as it is such an amount that the heat stability and/or oxidation stability of the para-methoxycinnamic ester contained can be enhanced, but the content is preferably 0.001 to 1% by mass, more preferably 0.004 to 0.5% by mass, most preferably 0.01 to 0.1% by mass, based on the para-methoxycinnamic ester contained. When the content is less than 0.001% by mass, sufficient heat stability effect and/or oxidation stability effect can not be obtained, and when it is more than 1% by mass, its influence on the hue of the ultraviolet absorber undesirably gets larger.

The invention further relates to a cosmetic comprising the above ultraviolet absorber. Other components than the ultraviolet absorber in the cosmetic of the invention are cosmetic components usually used, and not particularly limited.

Such cosmetic components usually used include solid, semisolid or liquid oils (natural animal or vegetable fats and oils, semisynthetic fats and oils, hydrocarbon oils, higher fatty acids, higher alcohols, ester oils, silicone oils, fluorine-containing oils, etc.), water, alcohols (lower alcohols, sugar alcohols, sterols, etc.), water soluble macromolecules (vegetable macromolecules such as gum arabic and tragacanth, microbic macromolecules such as xanthan gum and dextran, starch macromolecules such as carboxymethylstarch, cellulose macromolecules such as carboxymethyl-cellulose sodium, etc.), surfactants (various anionic, cationic, nonionic, and amphoteric surfactants), oil soluble gelatinizers (metallic soaps, dextrin fatty acid esters, sucrose fatty acid esters, etc.), powder (inorganic powder such as titanium oxide, magnesium carbonate, mica or hydroxyapatite, organic powder such as polyamide powder, etc.), color pigments, pearlescent pigments, humectants, antiseptics, pH-adjusting agents, chelating agents, refrigerants, antiinflammatory agents, skin care components (whitening agents, cell-activating agents, agents for facilitating blood flow, etc.), vitamins, etc.

The content of the ultraviolet absorber in the cosmetic of the invention is not particularly limited so long as it is such an amount that the desired ultraviolet absorption effect can be attained, but, usually, the content is preferably 1 to 20% by mass, more preferably 4 to 20% by mass, as the content in the cosmetic containing the ultraviolet absorber itself.

Although described detailedly in an example as shown later, in the test of deterioration with heating, the sample with no addition of a stabilizer, and the sample with the addition of butylhydroxytoluene (BHT) which has hitherto been used deteriorated in smell and hue in such a degree that they could not actually be used, whereas the sample with the addition of the stabilizer of the invention scarcely changed in smell and hue, which shows that the effect of the stabilizer was fully exerted.

Further, described detailedly in an example as shown later, it is seen from the analysis of the components after the test of deterioration with heating, that δ-tocopherol used in the invention inhibited decomposition of the ultraviolet absorbing component better than α-tocopherol which is a known stabilizer.

EXAMPLES

The invention is further described according to examples, but the invention should not be limited to these examples.

Example 1

As para-methoxycinnamic acid-containing ultraviolet absorbers, one comprising 2-ethylhexyl para-methoxycinnamate and δ-tocopherol of the invention as added in an amount of 0.05% by mass, one comprising 2-ethylhexyl para-methoxycinnamate and butylhydroxytoluene (BHT) as added in an amount of 0.05% by mass, and one comprising 2-ethylhexyl para-methoxycinnamate alone (i.e., no addition of a stabilizer; blank) were prepared and subjected to the CDM test (see "Analysis Test Methods for Standard Fats and Oils" edited by Japan Society of Oil Chemistry, 1996, 2.5.1.2-1996). The measurement temperature was 130° C. and the measurement time was up to 50 hours. The measurement results and the state of the samples are shown in Table 1.

The outline of the measurement method is as follows. The measurement sample is heated to the measurement temperature in a reaction vessel, while blowing clean air therein. Volatile decomposed substances formed by oxidation are captured in water, and the time of up to the inflection point where the electric conductivity of the water rapidly increases (induction time) is measured. And, the smell and color of the measurement sample immediately after the measurement of induction time are judged.

Criterion on the Smell

The smell before the measurement is ◉, and the smell gets stronger in order of ○→Δ→x.

Criterion on the Color

The color before the measurement is 1, and the coloring increases in order of 1→5 (5-stage assessment).

TABLE 1

| Sample | Induction time | Smell | Color |
|---|---|---|---|
| addition of δ-tocopherol | Large increase of the electric conductivity was not observed | ◉ | 2 |
| Addition of butylhydroxytoluene | 42.8 h | Δ | 5 |
| No addition of a stabilizer | 42.7 h | x | 5 |
| Sample before the measurement | — | ◉ | 1 |

As apparent from Table 1, when the stabilizer of the invention was added, enhancement of the heat stability and oxidation stability was observed, and the degree of deterioration in smell and coloring of the measurement sample after the test was small.

On the other hand, when butylhydroxytoluene (BHT) which has hitherto been used was added, there was no large difference in heat stability and oxidation stability compared with the blank test of no addition, and conspicuous superiority was not observed also in deterioration smell.

Example 2

Figure 2:
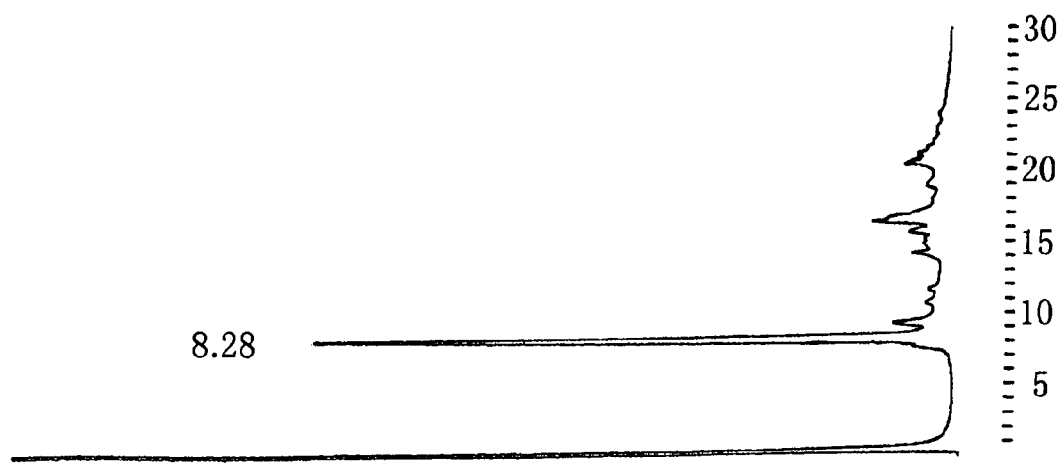
FIG. 2 shows the gas chromatogram of the measurement sample immediately after the CDM test on the case where α-tocopherol was added in an amount of 0.01% by mass.
Figure 3:
FIG. 3 shows the gas chromatogram of the measurement sample immediately after the CDM test on the case where δ-tocopherol was added in an amount of 0.005% by mass.
Figure 4:
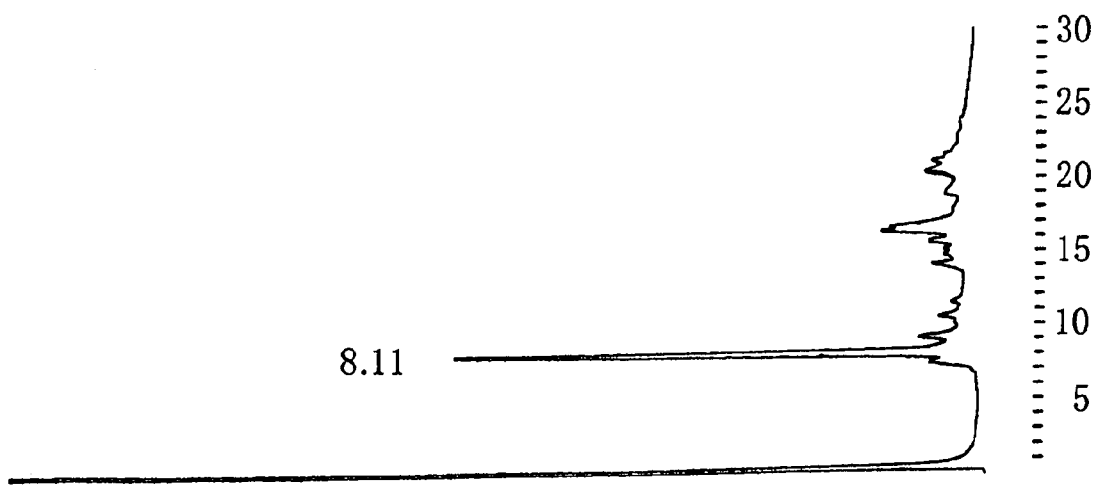
FIG. 4 shows the gas chromatogram of the measurement sample immediately after the CDM test on the case where α-tocopherol was added in an amount of 0.005% by mass.

As para-methoxycinnamic acid-containing ultraviolet absorbers, one comprising 2-ethylhexyl para-methoxycinnamate and δ-tocopherol of the invention as added in an amount of 0.01% by mass, one comprising 2-ethylhexyl para-methoxycinnamate and α-tocopherol as added in an amount of 0.01% by mass, one comprising 2-ethylhexyl para-methoxycinnamate and δ-tocopherol of the invention as added in an amount of 0.005% by mass, and one comprising 2-ethylhexyl para-methoxycinnamate and α-tocopherol as added in an amount of 0.005% by mass were prepared and subjected to the CDM test in the same manner as in Example 1. The measurement temperature was 130° C. and the measurement time was up to 100 hours. A measurement sample was taken from each of the ultraviolet absorbers immediately after the test, and subjected to gas chromatography for observing the change of the components after the test. The charts of the gas chromatography obtained are as shown in FIG. 1, FIG. 2, FIG. 3 and FIG. 4.

As apparent from comparison among FIGS. 1 to 4, the ultraviolet absorbers in which δ-tocopherol of the invention was added had a smaller proportion of decomposition of 2-ethylhexyl para-methoxycinnamate than the ultraviolet absorbers in which α-tocopherol was added in the same amount. Namely, the decomposition proportion in the case of 0.01% by mass addition was 24.7% in δ-tocopherol but 32.2% in α-tocopherol. Especially, the difference was clearer in the case of 0.005% by mass addition. Namely, the decomposition proportion in that case was 26.5% in δ-tocopherol and not so different from that in the case of 0.01% by mass addition, whereas the decomposition proportion in the case of 0.005% by mass addition was 48.0% in α-tocopherol. From the above, it is apparent that in a very small amount of addition δ-tocopherol of the invention is superior to known α-tocopherol in heat stability and oxidation stability.

INDUSTRIAL APPLICABILITY

As detailedly described above, δ-tocopherol used in the invention is very useful since it has a function to enhance the heat stability and/or oxidation stability of para-methoxycinnamic esters or ultraviolet absorbers containing the same, and decrease deterioration smell.

The invention claimed is:

1. An ultraviolet absorber comprising a para-methoxycinnamic ester, and δ-tocopherol in an amount of 0.001% by mass or more but less than 0.1% by mass based on the para-methoxycinnamic ester.

2. The ultraviolet absorber according to claim 1 wherein the para-methoxycinnamic ester is an alkyl para-methoxycinnamate in which the alkyl part is a straight-chain or branched-chain alkyl group having 1 to 18 carbon atoms, or glycerol di-para-methoxycinnamate mono-2-ethylhexanoate.

3. The ultraviolet absorber according to claim 1 wherein the para-methoxycinnamic ester is selected from the group consisting of ethyl para-methoxycinnamate, isopropyl para-methoxycinnamate, isoamyl para-methoxycinnamate, 2-ethylhexyl para-methoxycinnamate, and glycerol di-para-methoxycinnamate mono-2-ethylhexanoate.

4. The ultraviolet absorber according to claim 1 wherein the para-methoxy-cinnamic ester is 2-ethylhexyl para-methoxycinnamate.

5. The ultraviolet absorber according to claim 1 wherein the content of the para-methoxycinnamic ester in the ultraviolet absorber is 50% by mass or more.

6. The ultraviolet absorber according to claim 1 which contains, as additional components, a diluting or bulking component and/or another ultraviolet absorber.

7. A cosmetic comprising an ultraviolet absorber comprising a para-methoxycinnamic ester and δ-tocopherol in an amount of 0.001% by mass or more but less than 0.1% by mass based on the para-methoxycinnamic ester, and at least one cosmetic component.

8. The cosmetic according to claim 7 wherein the para-methoxycinnamic ester is an alkyl para-methoxycinnamate in which the alkyl part is a straight-chain or branched-chain alkyl group having 1 to 18 carbon atoms, or glycerol di-para-methoxycinnamate mono-2-ethyihexanoate.

9. The cosmetic according to claim 7 wherein the para-methoxycinnamic ester is selected from the group consisting of ethyl para-methoxycinnamate, isopropyl para-methoxycinnamate, isoamyl para-methoxycinnamate, 2-ethylhexyl para-methoxycinnamate, and glycerol di-para-methoxycinnamate mono-2-ethylhexanoate.

10. The cosmetic according to claim 7 wherein the para-methoxycinnamic ester is 2-ethyihexyl para-methoxycinnamate.

11. The cosmetic according to claim 7 wherein the content of the para-methoxycinnamic ester in the ultraviolet absorber is 50% by mass or more.

12. The cosmetic according to claim 7 wherein the content of the ultraviolet absorber in the cosmetic is 1 to 20% by mass.

13. A method for enhancing the heat stability and/or oxidation stability of a para-methoxycinnamic ester which method comprises contacting the para-methoxycinnamic ester with δ-tocopherol in an amount of 0.001% by mass or more but less than 0.1% by mass based on the para-methoxycinnamic ester.

14. The method according to claim 13 wherein the para-methoxycinnamic ester is an alkyl para-methoxycinnamate in which the alkyl part is a straight-chain or branched-chain alkyl group having 1 to 18 carbon atoms, or glycerol di-para-methoxycinnamate mono-2-ethylhexanoate.

15. The method according to claim 13 wherein the para-methoxycinnamic ester is selected from the group consisting of ethyl para-methoxycinnamate, isopropyl para-methoxycinnamate, isoamyl para-methoxycinnamate, 2-ethylhexyl para-methoxycinnamate, and glycerol di-para-methoxycinnamate mono-2-ethylhexanoate.

16. The method according to claim 13 wherein the para-methoxycinnamic ester is 2-ethylhexyl para-methoxycinnamate.

* * * * *